United States Patent
Chen et al.

(10) Patent No.: US 8,893,314 B2
(45) Date of Patent: Nov. 25, 2014

(54) SPORT GOGGLE WITH QUICK RELEASE LENS

(75) Inventors: Vic Chen, Dongshan Township, Yilan County (TW); Yestin Wang, Taichung (TW)

(73) Assignee: Dye Precision, Inc., San Diego, CA (US)

( * ) Notice: Subject to any disclaimer, the term of this patent is extended or adjusted under 35 U.S.C. 154(b) by 0 days.

(21) Appl. No.: 13/566,821

(22) Filed: Aug. 3, 2012

(65) Prior Publication Data

US 2014/0033408 A1 Feb. 6, 2014

(51) Int. Cl.
*A61F 9/02* (2006.01)
*G02C 5/22* (2006.01)
*G02C 5/00* (2006.01)

(52) U.S. Cl.
USPC ............... 2/441; 2/426; 2/434; 2/448; 2/450; 351/86; 351/116; 351/138; 351/154

(58) Field of Classification Search
None
See application file for complete search history.

(56) References Cited

U.S. PATENT DOCUMENTS

| | | | | |
|---|---|---|---|---|
| 4,865,437 A * | 9/1989 | Neuhaus | ...... | 351/116 |
| 5,018,223 A * | 5/1991 | Dawson et al. | ...... | 2/436 |
| 5,133,596 A * | 7/1992 | Korny et al. | ...... | 351/158 |
| 5,189,447 A * | 2/1993 | Oleson | ...... | 351/121 |
| 5,410,763 A * | 5/1995 | Bolle | ...... | 2/436 |
| 5,426,473 A * | 6/1995 | Riehm | ...... | 351/121 |
| 5,428,410 A * | 6/1995 | Lei | ...... | 351/47 |
| 5,542,130 A * | 8/1996 | Grabos et al. | ...... | 2/436 |
| 5,564,132 A * | 10/1996 | Kuo | ...... | 2/430 |
| 5,617,588 A * | 4/1997 | Canavan et al. | ...... | 2/428 |
| 5,642,530 A * | 7/1997 | Parks | ...... | 2/435 |
| 5,657,493 A * | 8/1997 | Ferrero et al. | ...... | 2/428 |
| 5,752,280 A * | 5/1998 | Hill | ...... | 2/453 |
| 5,764,330 A * | 6/1998 | Simioni | ...... | 351/41 |
| 5,790,230 A * | 8/1998 | Sved | ...... | 351/138 |
| 5,815,235 A * | 9/1998 | Runckel | ...... | 351/92 |
| 6,718,561 B2 * | 4/2004 | Dondero | ...... | 2/436 |
| 6,755,521 B1 * | 6/2004 | Begg | ...... | 351/48 |
| 6,886,183 B2 * | 5/2005 | DeHaan et al. | ...... | 2/6.7 |
| 6,948,813 B2 * | 9/2005 | Parks | ...... | 351/158 |
| 7,039,959 B2 * | 5/2006 | Dondero | ...... | 2/436 |
| 7,200,875 B2 * | 4/2007 | Dondero | ...... | 2/436 |
| 7,441,889 B2 * | 10/2008 | Zelman | ...... | 351/57 |
| RE41,834 E * | 10/2010 | Parks | ...... | 351/158 |
| 8,550,619 B2 * | 10/2013 | Walker et al. | ...... | 351/106 |
| 2002/0157175 A1 * | 10/2002 | Dondero | ...... | 2/436 |
| 2004/0060101 A1 * | 4/2004 | Shiue | ...... | 2/426 |
| 2004/0083540 A1 * | 5/2004 | Dondero | ...... | 2/436 |
| 2005/0015862 A1 * | 1/2005 | Dondero | ...... | 2/436 |
| 2006/0072066 A1 * | 4/2006 | Mihelic | ...... | 351/41 |
| 2007/0258037 A1 * | 11/2007 | Zelman | ...... | 351/41 |
| 2008/0143951 A1 * | 6/2008 | Won | ...... | 351/57 |
| 2009/0190088 A1 * | 7/2009 | Strobel | ...... | 351/63 |
| 2012/0147316 A1 * | 6/2012 | Loeb et al. | ...... | 351/55 |
| 2012/0147317 A1 * | 6/2012 | Loeb et al. | ...... | 351/55 |
| 2012/0320331 A1 * | 12/2012 | Walker et al. | ...... | 351/57 |

* cited by examiner

*Primary Examiner* — Bobby Muromoto, Jr.
(74) *Attorney, Agent, or Firm* — Knobbe Martens Olson & Bear LLP

(57) ABSTRACT

Disclosed is a sport goggle that includes a latching mechanism for a user to quickly release a lens from a frame without tools. The lens is released from the frame by pressing a button surface which bends a spring member in the frame unlocking the lens.

19 Claims, 9 Drawing Sheets

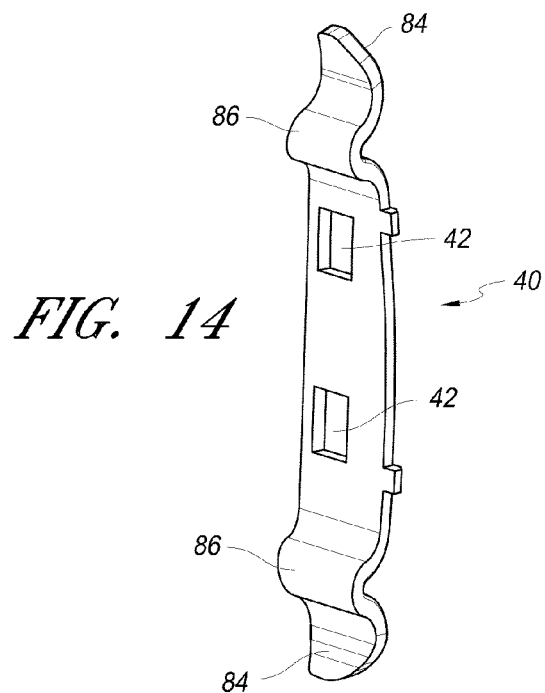
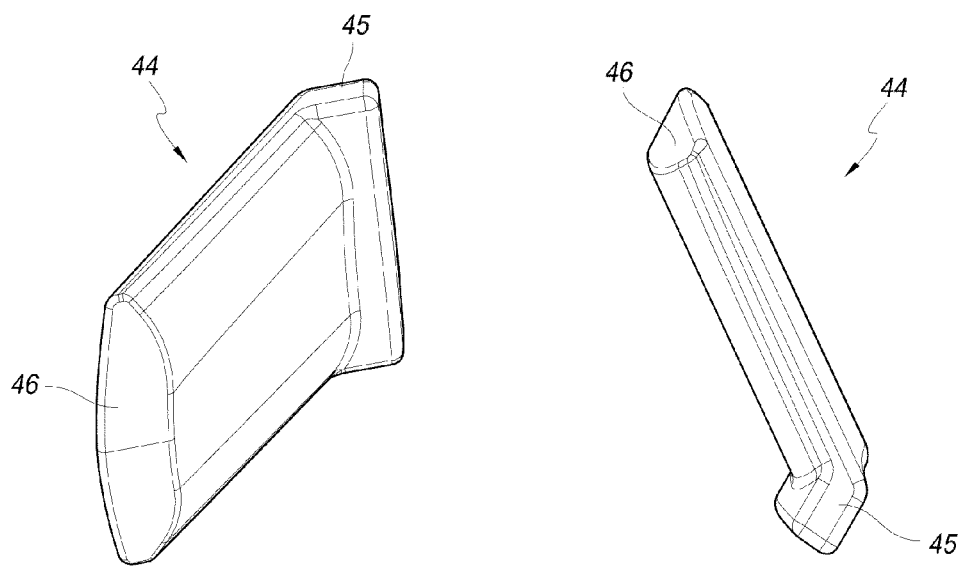
FIG. 14
FIG. 15     FIG. 16

SPORT GOGGLE WITH QUICK RELEASE LENS

BACKGROUND

1. Field

This disclosure relates in general to eyewear and more particularly to sport goggles with a frame having a releasably mounted lens.

2. Description of the Related Art

Most goggles have problems with difficulty of assembly and disassembly for cleaning, sub-optimal vision through the lens, sub-optimal ventilation through the goggle, and sub-optimal comfort. For example, numerous patents have proposed various systems for protecting the eyes of a person from debris (e.g., snow, mud, paintballs, dirt, rock, etc.) entering the eyes of the participant. For example, in environments and situations in which the person is at risk for injury to the eyes or face from impact by high velocity debris such as when playing paintball, a sport goggle can protect the eyes. In other sport where impact is by debris travelling at lower velocities than a paintball such as when snowboarding, the sport goggle not only protects the eye but also can include optics which are intended to enhance the contrast of the wearer's surroundings/environment.

A snowboarder may have a sport or snow goggle strapped around his/her face or head. The snow goggle has a frame which holds at least a partially transparent lens through which the wearer may view his/her surroundings/environment and by which snowflakes or snow are prevented from entering into the wearer's eyes. While snowboarding, the inner surface of the lens is spaced from the wearer's face. Heat from the wearer's face warms the lens beginning at the inner surface of the lens and continuing through the lens towards the outer surface of the lens. This warming of the lens may result in the outer surface being warmer than the ambient temperature. When outside snowflakes land on the outer surface of the lens they melt requiring the user to wipe the lens. This continuing process of wiping the lens to remove melted snow can obscure the user's view through the lens by scratching the lens. The scratched lens may prevent the snowboarder from clearly seeing his/her environment. Another source of scratches is from storing the sport goggles without a cover. In this instance, the lens of the goggle may be placed on a tabletop or within a bag. Contents within the bag and the tabletop surface may itself scratch the exterior surface of the lens.

Further, a specific lens combination may be preferred by the wearer depending on the current weather to enhance their view of the ski slope. In snowboarding applications, interchangeability of lenses is desired due to different environmental conditions that the wearer may encounter. For example, the different environments may warrant different levels of light attenuation and/or color filtration. There have been numerous attempts to provide goggles adaptable for snowboarding with interchangeable lenses of different colors to provide the optimal vision, despite the often variable atmospheric and light conditions that may be encountered by a snowboarder in the course of even a single day. On some snow goggles, the lenses are interchangeable only with the use of special tools by a trained professional. Other such snow goggles include a flexible frame that must be deformed in order to remove and insert the different lenses. For example, the lens can fit into the frame with a slight interference fit induced by making the circumference around the edge of the lens slightly longer than a corresponding path along a lens groove in the frame. Thus, in a frame of this design, a lens generally cannot be freely installed in or removed from the frame. Further, while it is possible to manually change such lenses when the user's fingers are warm in a controlled environment, such is generally not the case when one is on the ski slopes. Fingers are often numb or clad in gloves, reducing manual dexterity to a minimum and making the changing of lenses in the goggles extremely difficult. Further, when such lenses are not properly mounted in the frame, the lens may become dislodged, resulting in possible loss of the lens and, even worse, direct or indirect injury to the wearer. Further, fashion also plays a role in lens tint and color selection for many snowboarders.

Another deficiency, in prior art sport goggles, is the discomfort in wearing the sport goggle. The sport goggle is uncomfortable to wear due to the manner in which the sport goggle is secured to the face of the wearer. In particular, the sport goggle may comprise an elastic head strap. The lens and frame of the sport goggle are disposed in front of the wearer's face while the head strap is routed to the rear of the wearer's head. The head strap is tensioned such that the frame is pressed against the wearer's face. The head strap is attached to the lateral sides of the frame. The tension of the head strap pulls on the lateral sides of the frame and presses the sport goggle unevenly against the wearer's face. The uneven pressure against the wearer's face is one source of discomfort.

In view of the foregoing, a need exists for an improved sport goggle.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description of Certain Embodiments," one will understand how the features of the embodiments described herein provide advantages over other sport goggles.

An aspect of the disclosure is directed to a sports goggle having a frame defining a field of view for a wearer and a strap attachable to lateral ends of the frame and configured to circumscribe a head of the wearer. The goggle further includes a first lens attachable to the frame and a second lens attachable to the frame and covering the first lens. The second lens having one or more first engagement members projecting away from an inner surface of the second lens. The goggle further includes a second engagement member disposed on the frame and configured to selectively engage with the first engagement member. The second engagement member having a button surface and being movable between a locked position and an unlocked position. The second engagement member engaging with the first engagement member when in the locked position to prevent the second lens from being removed from the frame. The second engagement member disengaging from the first engagement member when the button surface is pressed by the wearer.

Another aspect of the disclosure is a sports goggle having a frame defining a field of view for a wearer. The frame including an outer frame member releasably securable to an inner frame member. The outer frame member having a passage extending through a side of the outer frame. The inner frame member including one or more tangs extending from the inner frame member so as to enter the passage when the inner frame is secured to the outer frame. The goggle including a strap having connectors at both ends of the strap. The connectors being attachable to lateral ends of the outer frame member. Each connector having one or more projections. The projections being configured to enter the passage in the outer frame member from an opposite side from the one or more tangs to engage with the tangs of the inner frame member.

Another aspect of the disclosure is a sports goggle having a frame defining a field of view for a wearer and having a spring member and an actuator bar. The actuator bar being disposed in the frame and slidable between a first position and a second position. The spring member being disposed in the frame so as to bend between a locked position and an unlocked position. The spring member being in the locked position when the actuator bar is in the first position and being in the unlocked position when the actuator bar is in the second position. The goggle further including a lens attachable to the frame and having one or more tabs projecting away from an inner surface of the lens. The tabs engaging with the spring member when the actuator bar is in the first position to prevent the lens from being removed from the frame. The tabs disengaging from the spring member when the actuator bar is slid to the second position.

BRIEF DESCRIPTION OF THE DRAWINGS

These and other features, aspects and advantages of the present invention will now be described in connection with certain embodiments of the invention, in reference to the accompanying drawings. The illustrated embodiments, however, are merely examples and are not intended to limit the invention. The following are brief descriptions of the drawings.

FIG. 14 is a front perspective view of a spring member from the latching mechanism which is actuated by a button to disengage the outer lens from the outer frame, FIG. 15 is a perspective end view of the actuator bar from FIG. 13, and FIG. 16 is a perspective side view of the actuator bar from FIG. 13.

DETAILED DESCRIPTION OF CERTAIN EMBODIMENTS

Figure 1:
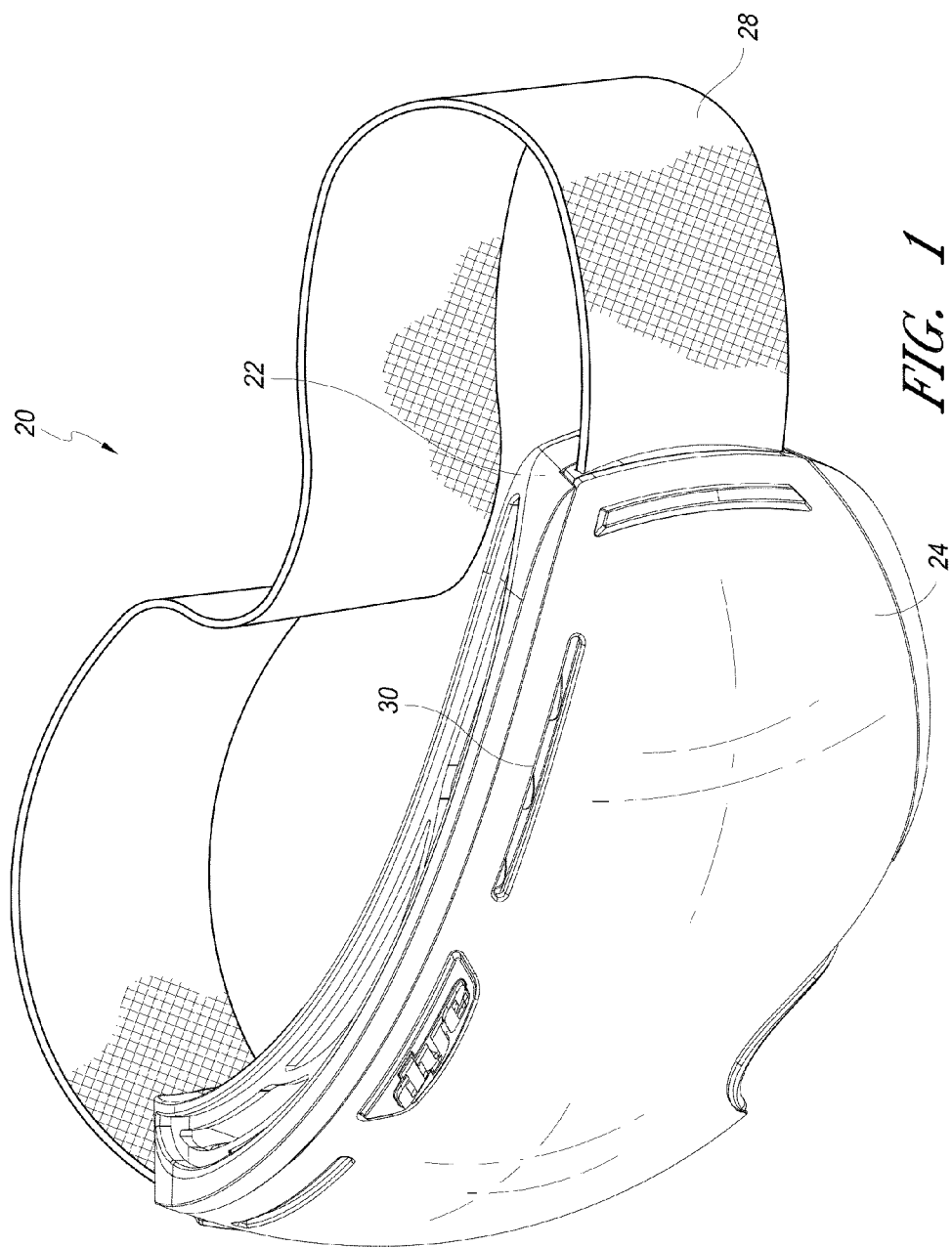
FIG. 1 is a perspective view of a sport goggle in accordance a preferred embodiment of the present invention which includes a frame, one or more lens, and a strap.

FIG. 1 is a perspective view of a sport goggle 20 in accordance a preferred embodiment of the present invention. The sport goggle 20 includes a frame 22, one or more lenses 24, 26, and a strap 28. The one or more lenses 24, 26 may have any suitable shape or structure and may be made from any material.

Figure 2:
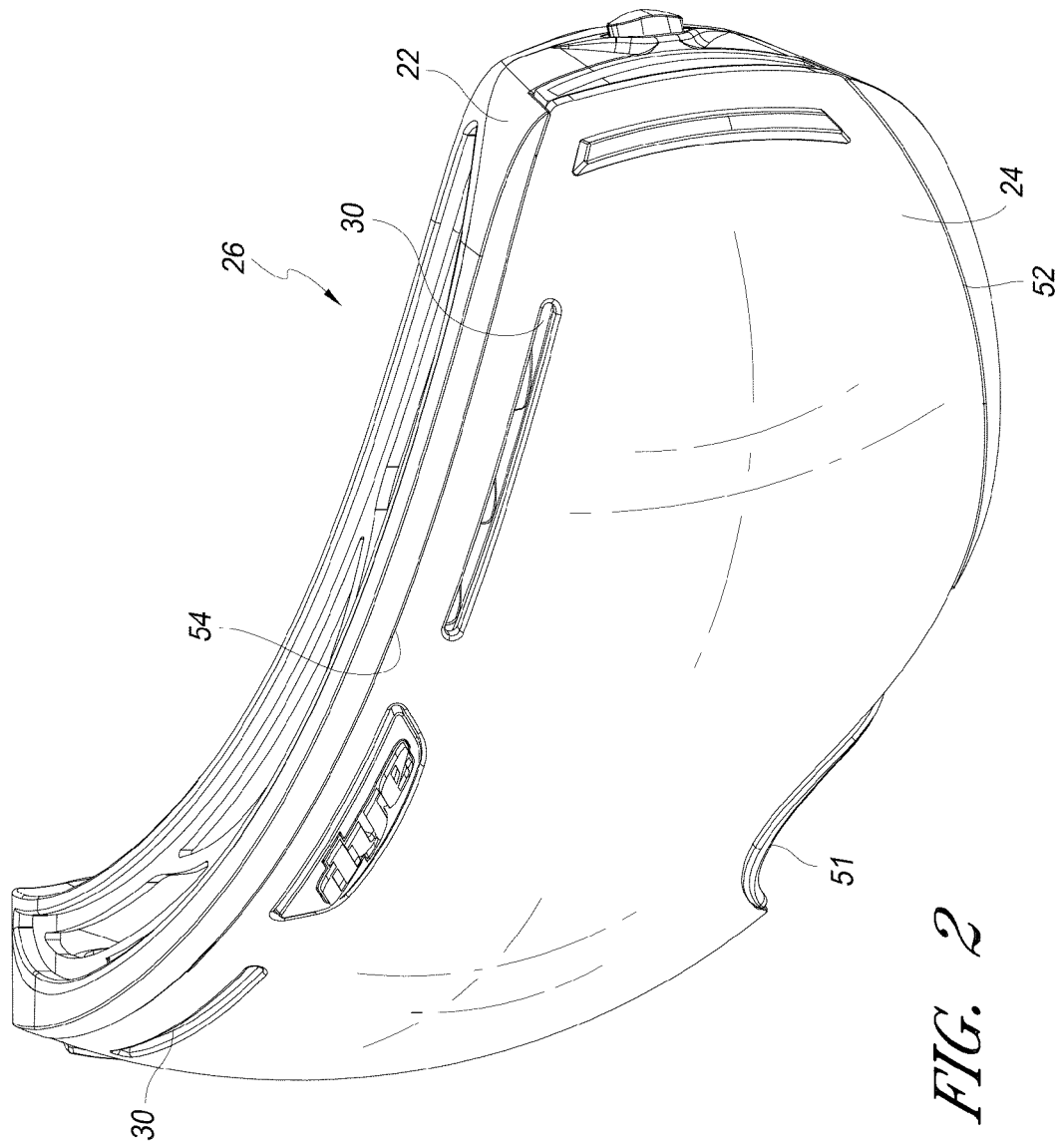
FIG. 2 is a perspective view of the sport goggle illustrated in FIG. 1 with the strap removed.

FIG. 2 is a perspective view of the sport goggle 20 illustrated in FIG. 1 with the strap 28 removed so as to more clearly show the outer periphery of the frame 22. The strap is used to secure and properly position the goggle 20 on the head of a user. Alternatively, the goggle 20 can include arms. The arms may be pivotally attached to the lateral ends of the frame 22 and engage the head of a user when the goggle 20 is properly positioned over the facial region. Although the embodiment of the goggle 20 illustrated in FIG. 2 includes a strap 28, the goggle 20 may include any suitable mechanism or components for securely positioning the frame 22 on the head of a user. Accordingly, in alternate embodiments, the frame 22 may include arms instead of the strap 28.

In the embodiment illustrated in FIGS. 1 and 2, the sport goggle 20 includes an outer lens 24 and an inner lens 26. Preferably the outer lens 24 is spaced from the inner lens 26 to define an air gap between the inner and outer lenses 24, 26. The air gap thermally insulates the face of the wearer from the outer lens 24. By thermally insulating the outer lens 24, snow is less likely to melt on the outer surface of the outer lens 24 and condensation is less likely to form on the inner surface of the inner lens 26. In this way, a double lens structure may be desirable to prevent fogging or provide extra ultra-violet (UV) protection. In certain embodiments, the sport goggle 20 includes only a single lens which forms a shield across frame 22. One or more vents 30 can also be included in the outer lens 24 and/or frame 22 to provide air flow into the air gap between the inner lens 26 and the outer lens 24.

Even though many of the advantages set forth herein are specific to cold weather sport such as snowboarding, the use of the inventive sport goggle 20 is not limited to any particular sport or use. For example, the one or more lenses 24, 26 may serve various functions including magnifying images, protecting the facial region of a user, correcting vision (prismatic power, astigmatism, etc.), and attenuating sunlight. The one or more lenses 24, 26 may be manufactured from a variety of materials including, but not limited to, polycarbonate or acrylic. The one or more lenses 24, 26 may be photochromatic, polarized, or tinted to provide a range of light attenuation, color filtration, and vision correction. It should be noted that the various embodiments of the one or more lenses 24, 26 are exemplary and are not intended to limit the scope of the present disclosure in anyway.

Figure 3:
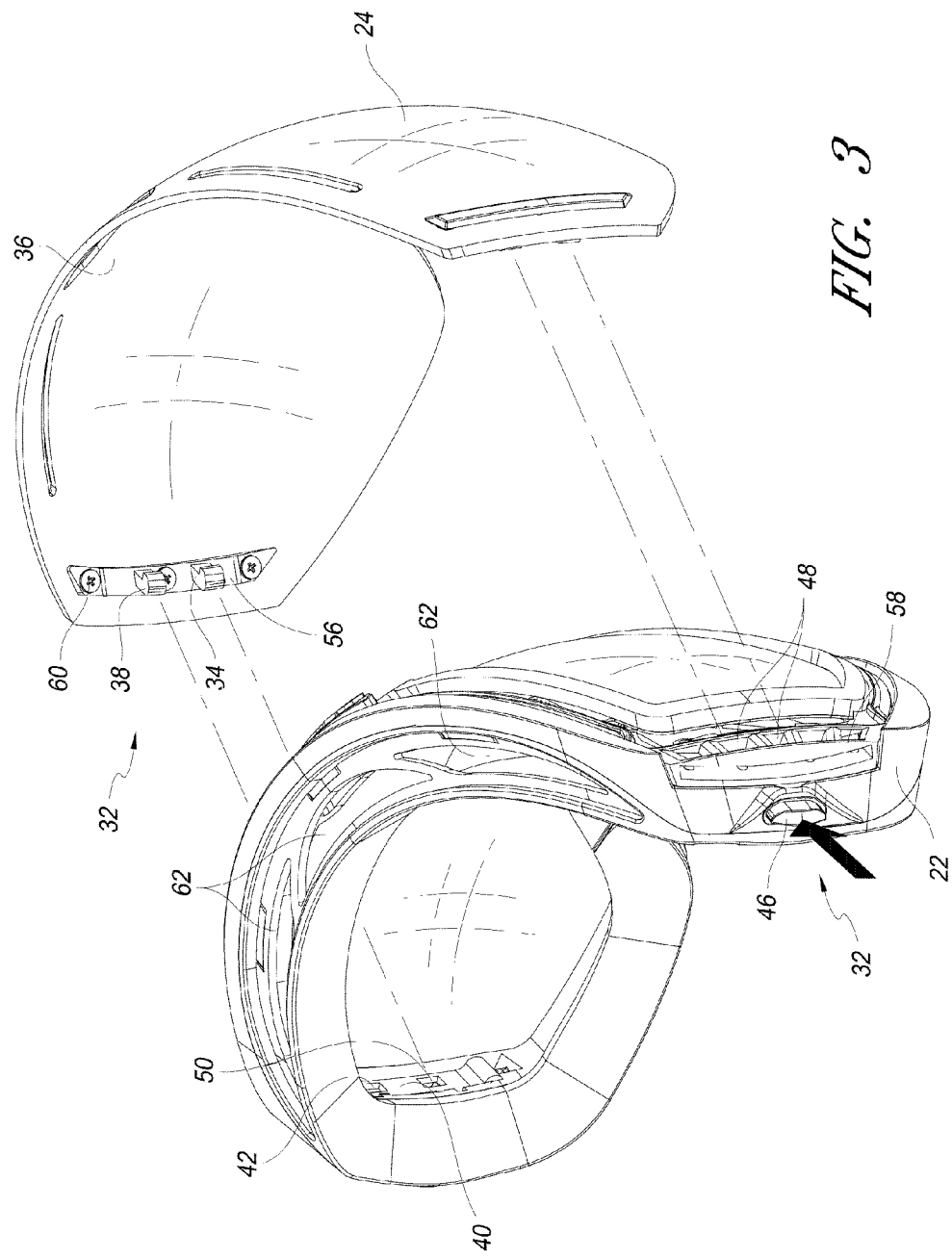
FIG. 3 is a rear perspective view of the sport goggle illustrated in FIG. 2 with an outer lens removed from the frame by actuating one or more latching mechanisms and exposing an outer surface of the inner lens of the sport goggle.

FIG. 3 is a rear perspective view of the sport goggle 20 illustrated in FIG. 2 with the outer lens 24 removed from the frame 22 by actuating one or more quick release latching mechanisms 32 on the frame 22. The latching mechanism 32 is components which may releasably secure one or more lenses 24, 26 in the frame 22. In particular, the latching mechanism 32 may shift between open/unlocked and closed/ locked positions to release and secure lenses 24, 26 in frame 22. When in the locked position, the latching mechanism 32 may engage one or more lenses 24, 26 and thereby apply a force which places the one or more lenses 24, 26 in compression and a portion of the frame 22 in tension. The paired compressive and tensile forces may induce an interference fit wherein the one or more lenses 24, 26 is securely retained by the frame 22. By contrast, when the latching mechanism 32 is moved to the unlocked position the applied force is released and a tab is retracted allowing for removal of the one or more lenses 24, 26 from the frame 22.

In the illustrated embodiment, only the outer lens 24 is secured by the latching mechanism 32. However, the disclosure is not limited to the illustrated embodiment. Accordingly, the frame 22 may employ a latching mechanism 32 for the inner lens 26. With the outer lens 24 removed, the outer surface of the inner lens 26 of the sport goggle 20 is exposed.

Thus, the one or more lenses 24, 26 of the sport goggle 20 may be replaceable and thus readily removable from the frame 22. More particularly, the one or more quick release latching mechanism 32 disposed on the frame 22 and/or lenses 24, 26 selectively retains at least a portion of the one or more lenses 24, 26 relative to the frame 22.

A variety of latching mechanisms are possible. The latching mechanism 32 may be disposed partially on the frame 22 and partially on the outer lens 24, or entirely on one or the other component. It can be integrally formed with the goggle 20, or may be separate components which are formed separately and attached to the goggle 20.

In the illustrated embodiment, sport goggle 20 includes two latching mechanisms 32 disposed near temple regions of the frame 22 for securing, at least in part, the outer lens 24 to the frame 22. Of course one or both of the inner and outer lenses 24, 26 may be secured at least in part by one or more latching mechanisms 32 without falling outside the scope of the invention. Further, the latching mechanism 32 need not be disposed at any particular location as long as the latching mechanism 32 secures at least a portion of one of the one or more lenses 24, 26 to at least a portion of the frame 22.

According to certain embodiments, the latching mechanism 32 includes a first engagement structure and a second engagement structure. One of the first and second engagement structures is preferably disposed on the outer lens 24 while the other one of the first and second engagement structures is disposed on the frame 22 so that the first and second engagement structures selectively secure at least the outer lens 24 to the frame 22.

In the illustrated embodiment, the first engagement structure is in the form of one or more tabs 34 projecting from an inner surface 36 of the outer lens 24. The exemplary outer lens 24 illustrated in FIG. 3 includes four tabs 34 of which two tabs 34 are each disposed in the temple regions of the outer lens 24. Each tab 34 extends away from the outer lens 24, and is topped by a hook 38. Each hook 38 includes a portion which curves away from the tab 34. In certain embodiments, the tabs 34 approach the second engagement structure along a path that is approximately tangent to the outer lens 24 when the outer lens 24 is moved towards the frame 22. This directional motion may apply a compressive force on the outer lens 24 without directly imparting non-tangential forces to the outer lens 24 surface. The application of non-tangential forces may cause optical distortion and premature cracking of the outer lens 24. Desirably, an upper end of the tab 34 is relatively blunt and smooth to prevent them from puncturing or snagging the gloves or skin when a user is removing or replacing the outer lens 24.

In the illustrated embodiment, the second engagement structure is in the form of one or more spring members 40 in the frame 22. The spring member 40 may be integral with the frame 22 or as illustrated in FIG. 3 or a separate member disposed within the frame 22. However, any number of tabs 34 and spring members 40 may be used, and their disposition between the outer lens 24 and the frame 22 may be reversed or mixed. Each spring member 40 includes one or more receptacles 42 which are disposed so as to engage with at least a portion of the hook 38 on the tab 34.

The latching mechanism 32 further includes an actuator bar 44. In the illustrated embodiment the actuator bar 44 is disposed in the frame 24 and forms an extension of the spring member 40 in a direction towards an outer surface of the frame 24. The actuator bar 44 includes a button surface 46 that when pressed slides the actuator bar 44 towards the spring member 40. The button surface 46 may comprise a plate or other appropriate surface disposed roughly perpendicular to the translation axis of the actuator bar 44. The button surface 46 may protrude above the outer surface of the frame 22 at least when in a non-actuated state. Preferably, the spring member 40 forces the actuator bar 44 to protrude above the outer surface of the frame 22 when the button surface 46 is not being pressed by the user.

The actuator bar 44 includes a hooked shaped end 45 which prevents the actuator bar 44 from being removed from the frame 22 in a direction away from the spring member 40. The end 45 of the actuator bar 44 abuts against a facing surface on the frame 22 when the actuator bar 44 is in the non-actuated state.

The length of the actuator bar 44 allows the button surface 46 to be disposed at a position which is beyond the outer surface of the frame 22 of the goggle 20 at least when the latching mechanism 32 secures the outer lens 24 to the frame 22. This may be advantageous in that the button surface 46 may be manipulated by a user more easily if it protrudes beyond the outer surface of the frame 22, eliminating the need for precise positioning or pressure when releasing the latching mechanism 32, as will be described below.

When the latching mechanism 32 is positioned in the locked position, the tab 34 may fully engage the spring member 40 and thereby create an obstruction to the escape of the tab 34, as well as apply a compressive force to the outer lens 24. The application of the compressive force and/or the obstruction may secure the outer lens 24 in the frame 22.

In certain embodiments, when inward pressure is exerted upon the button surface 46 of the latching mechanism latch 32, the force is transferred from the button surface 46 through the actuator bar 44 and in a direction towards the spring member 40. The actuator bar 44 may be in contact with the spring member 40 when in the non-actuated state or a gap may exist between the spring member 40 and the actuator bar 44 when in the non-actuated state. For embodiments which have a gap, when the button surface 46 is pressed the actuator bar 44 initially translates or slides towards the spring member 40 until the actuator bar 44 contacts the spring member 40.

Figure 12B:
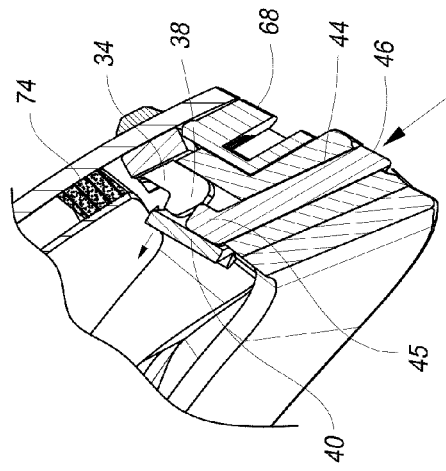
FIG. 12B is the same as FIG. 12A except that the latching mechanism is in the unlocked position to allow the outer lens to be removed from the outer member of the frame.
Figure 12A:
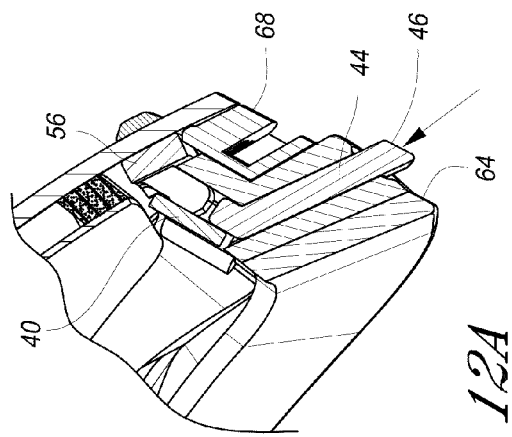
FIG. 12A is a partial fragmentary view of a portion of the frame and the one or more lens with the latching mechanism for the outer lens in a locked position.

Once the actuator bar 44 contacts the spring member 40, further force applied to the button surface 46 presses the actuator bar 44 into the spring member 40, causing the spring member 40 to flex inwardly away from the hooks 38 on the tabs 34 of the outer lens 24. As can be seen in FIGS. 12A-12B, as the actuator bar 44 moves inwardly, the spring member 40 is deflected away from the tabs 34. This action may clear a removal path for the tabs 34 as well as release a compressive force applied by the latching mechanism 32 to secure the outer lens 24 to the frame 22.

The button surface 46 may have an angled outer surface such that this surface slopes from front to back. Such positioning may be advantageous in minimizing unintentional disengagement of the latching mechanism 32 due to inadvertent contact with tree branches, picnic tables, or the like.

In order to interoperate with the latching mechanism 32, appropriate receptacles 42 for the tabs 34 are disposed upon the spring member 40 of the frame 22. As seen in FIG. 3, each spring member 40 may comprise two receptacles 42. In the illustrated embodiment, these receptacles 42 extend through the entire thickness of the spring member 40, forming holes through the spring member 40. Those of skill in the art will recognize that the holes need not extend entirely through the spring member 40 in alternate embodiments making use of appropriately sized tabs 34.

The positioning of the receptacles 42 upon the spring member 40 is desirably such that they lie in a position beneath the tabs 34 of the latching mechanism 32 when the outer lens 24 is moved over the frame 22 towards a secured position (see FIG. 3). In the illustrated embodiment, the position of the receptacles 42 is also roughly the same as the position of passages 48 which extend through the frame 22 and receive the tabs 34.

The receptacles 42 may further comprise a shelf 50, disposed within the receptacle 42. The shelf 50 may be angled slightly so that the upper surface of the shelf 50 (when the outer lens 24 is secured to the frame 24 as in FIG. 2) angles upwardly as it extends away from the tab 34 and towards the inside of the sport goggle 20. The hook 38 of the tab 34 will rest upon the shelf 50 of the receptacle 42 in order to secure the outer lens 24 in position upon the frame 22 of the sport goggle 20.

The frame 22 may further include one or more ridges or gutters for supporting the inner and outer lenses 24, 26 when the lenses 24, 26 are secured to the frame 22. In the illustrated embodiment, the frame 22 includes a nose gutter 51 for receiving a lower portion of the outer lens 24. The nose gutter 51 preferably wraps about a portion of the lower edge of the outer lens 24.

The frame 22 further includes ridges 52, 54. The ridges 52, 54 define surfaces which abut the upper and lower edges of the outer lens 24. The upper ridge 54 extends along an upper side of the goggle 20 while the lower ridge 52 extends along a lower side of the goggle 20. In the illustrated embodiment, the lower ridge 52 is separated into two lower ridges by the nose gutter 51.

The inner surface of the outer lens 24 may further include a platform 56. The platform 56 is received in a receiver 58 in the frame 22. The platform 56 preferably has a size and shape which is complementary to the size and shape of the receiver 58 so as to assist in positioning and securing the outer lens 24 on the frame 22. In the illustrated embodiment, the tabs 34 extend from a top surface of the platform 56. However, the tabs 34 need not be disposed on the platform 56 and may instead be located at a different position on the inner surface of the outer lens 24. The platform 56 is secured to the outer lens 24 by one or more fasteners 60 as is known in the art. The frame 22 includes a plurality of vent holes or vanes 62 to allow air to pass through the goggle 20. The vent holes or vanes 62 may be of any size, shape, or location.

Figure 4:
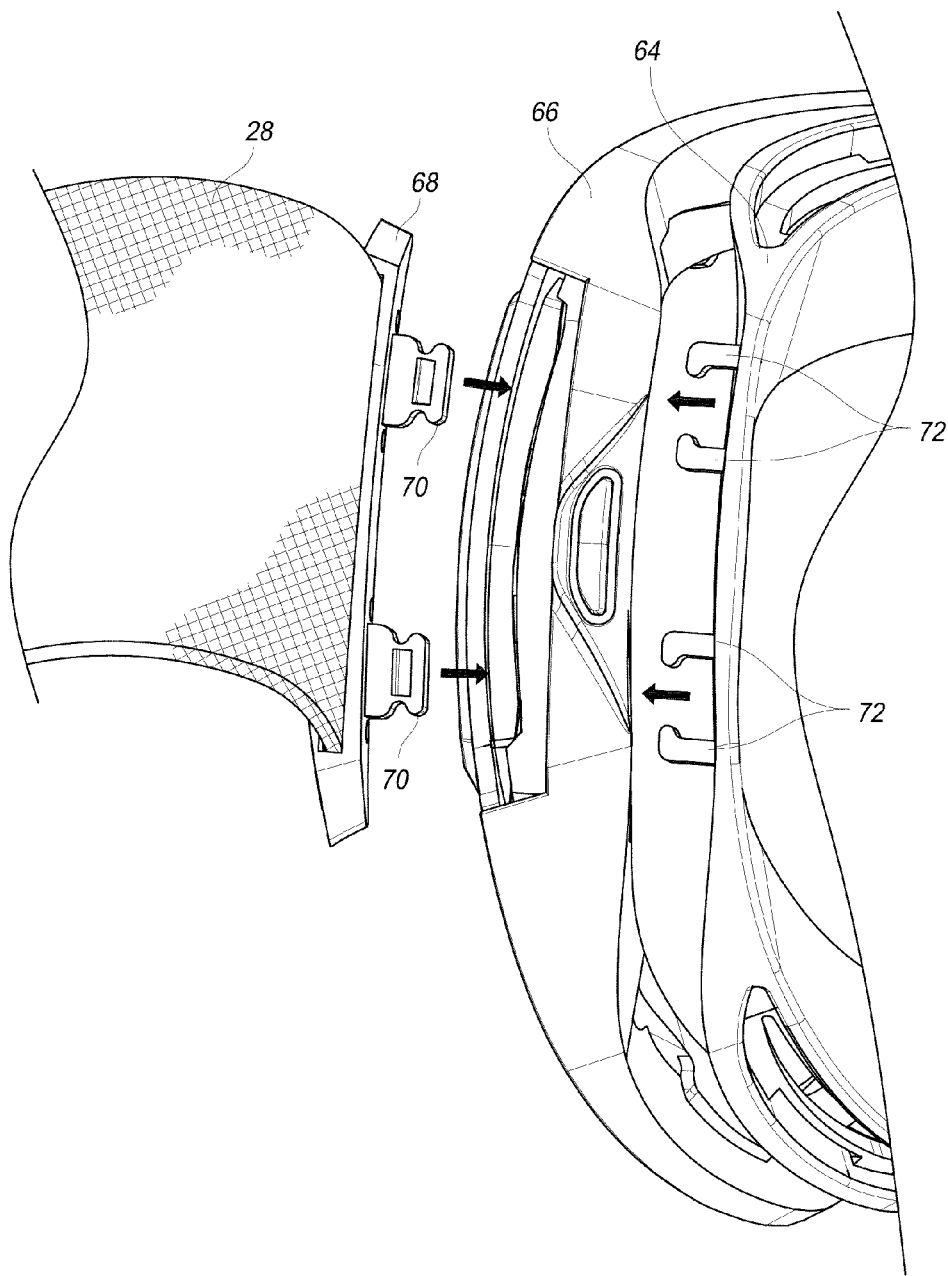
FIG. 4 is an exploded view of the temple region of the sport goggle from FIG. 1 showing an outer member of the frame disengaged from both an inner member of the frame and the strap.

FIG. 4 is an exploded view of the temple region of the sport goggle 20 from FIG. 1 showing an inner member 64 of the frame 22 disengaged from both an outer member 66 of the frame 22 and the strap 28. Each end of the strap 28 includes a connector 68 for securing to the frame 22. Each connector 68 includes one or more projections 70 which are disposed so as to extend into a passageway in the outer member 66 when the connector 68 abuts the outer member 66.

The inner member 64 includes one or more tangs 72 which extend into the same passageway but from the opposite end of the passageway when the inner member 64 abuts the outer member 66. When both the connector 68 and the inner member 64 abut opposite sides of the outer member 66, each of the one or more projections 70 are secured between a pair of the tangs 72 which secures the end of the strap 28 to the frame 22. This same arrangement for securing the outer member 66 to the inner member 64 with the connector 68 is employed on the other end of the frame 22 opposite to the end illustrated in FIG. 4. Thus, both ends of the strap 28 are secure in the same way to opposite ends of the frame 22.

Figure 5:
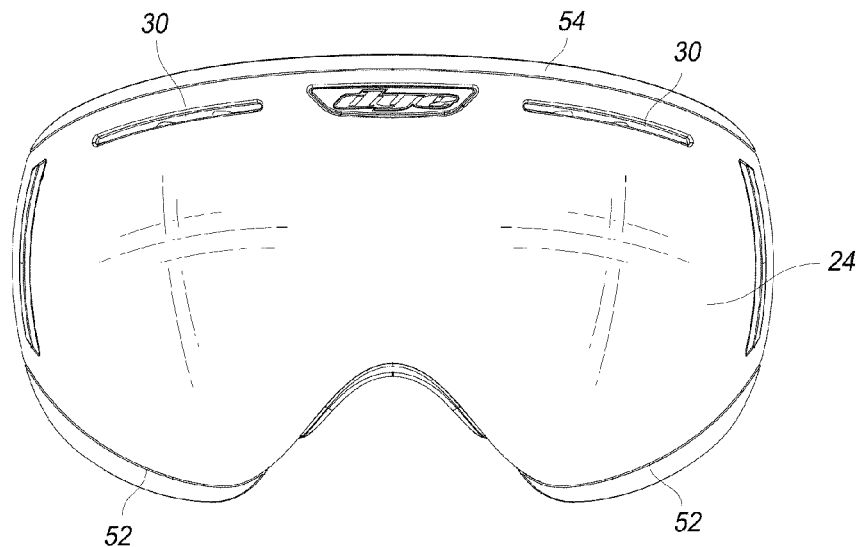
FIG. 5 is a front view of the sport goggle illustrated in FIG. 1 with the strap removed.
Figure 6:
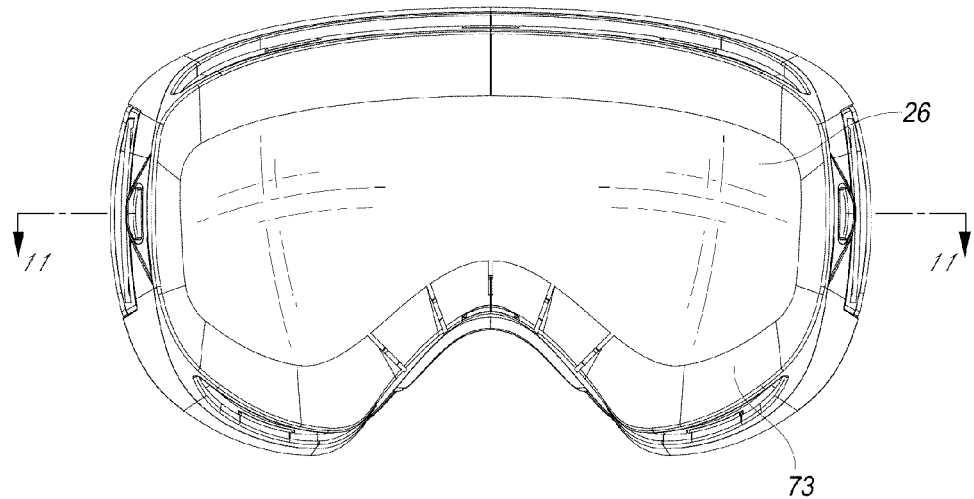
FIG. 6 is a back view of the sport goggle illustrated in FIG. 1 with the strap removed.

FIGS. 5 and 6 are front and back views of the sport goggle 20, respectively, with the strap 28 removed. As is illustrated in FIG. 6, an inside surface of the frame 22 includes foam 73 or other soft compressible material for contacting the wearer's face.

Figure 9:
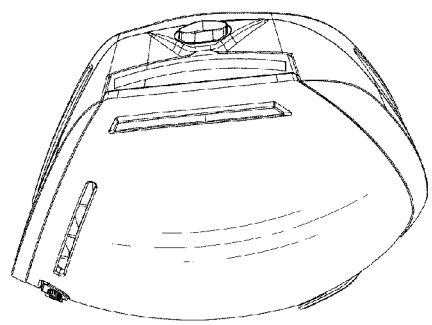
FIG. 9 is a first side view of the sport goggle illustrated in FIG. 1 with the strap removed.
Figure 10:
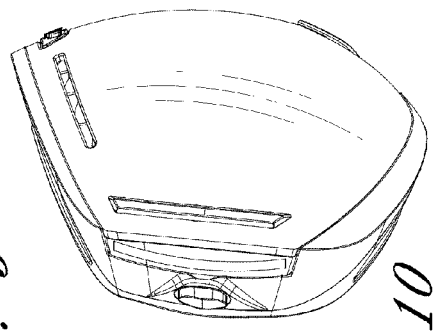
FIG. 10 is an opposite side view from FIG. 9 of the sport goggle illustrated in FIG. 1 with the strap removed.
Figure 7:
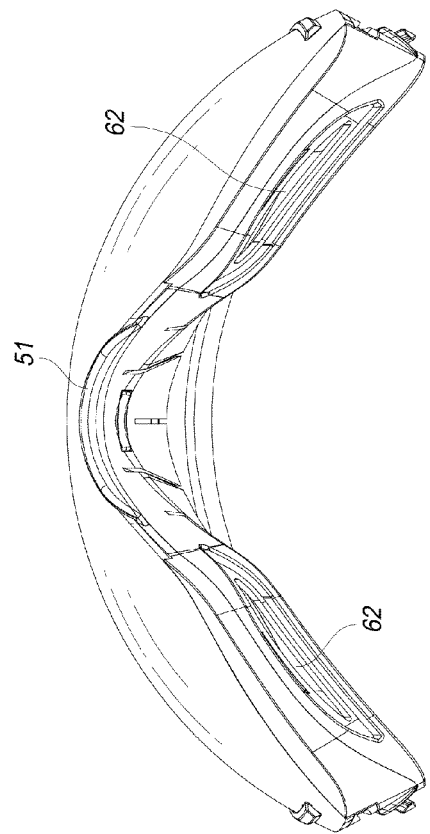
FIG. 7 is a bottom view of the sport goggle illustrated in FIG. 1 with the strap removed.
Figure 8:
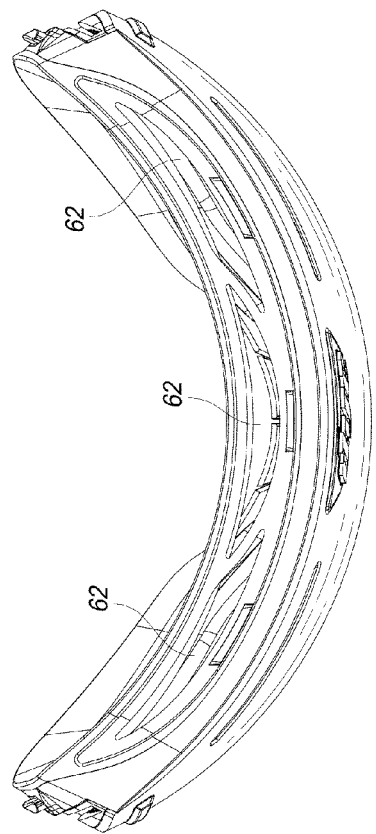
FIG. 8 is a top view of the sport goggle illustrated in FIG. 1 with the strap removed.

FIGS. 7 and 8 are bottom and top views of the sport goggle 20, respectively, with the strap 28 removed showing a plurality of vent holes or vanes 62. FIGS. 9 and 10 are side views of the sport goggle 20 illustrated in FIG. 1 with the strap 28 removed.

Figure 11:
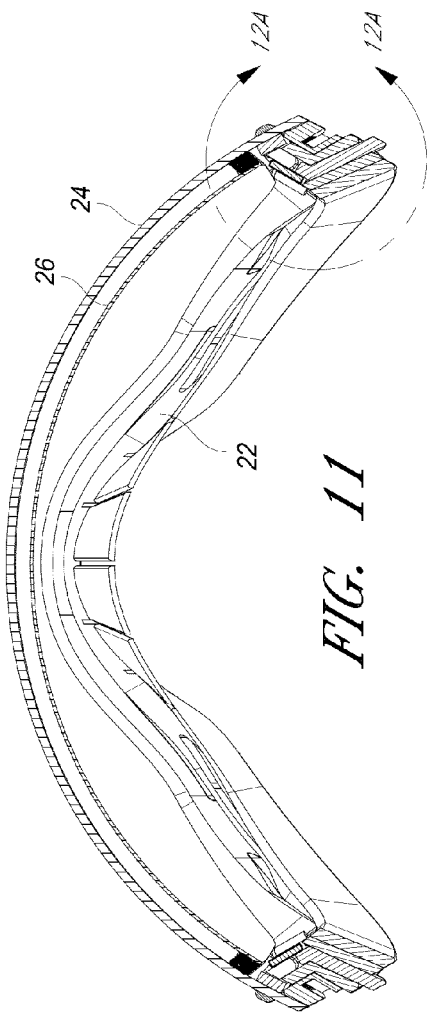
FIG. 11 is a cross-sectional view of the frame and the at least one lens of the sport goggle taken along line 11-11 of FIG. 6.

FIG. 11 is a cross-sectional view of the frame 22 and the at least one lenses 24, 26 of the sport goggle 20 taken along line 11-11 of FIG. 6. The goggle 20 includes a gasket 74 disposed in the frame 22 between the outer surface of the inner lens 26 and the inner surface of the outer lens 24. The gasket 74 defines the air gap between the lenses 24, 26 and further provides a surface against which the outer periphery of the outer lens 24 rests against when secured to the frame 22. In the illustrated embodiment, a first side of the gasket 72 contacts the extreme outer periphery of the inner lens 26. The side of the gasket 72 opposite from the first side contacts the outer lens 24 in a region which is inset from the extreme outer periphery of the outer lens 24. In this way the extreme outer periphery of the outer lens 24 in the temple region is available to abut the connector 68. The gasket 72 may be continuous or broken into multiple pieces. Further, the gasket 72 need not be continuous and can form gaps between adjacent ends of multiple pieces of the gasket 72. The platform 56 on the inner surface of the outer lens 24 abuts the connector 68.

FIG. 12A is a partial fragmentary view of a portion of the frame 22 and the one or more lenses 24, 26 with the latching mechanism 32 for the outer lens 24 is in a locked position. When in the locked position, the hooks 38 on the tabs 34 engage with the receptacles 42 in the spring member 40. FIG. 12B is the same as FIG. 12A except that the latching mechanism 32 is in the unlocked position to allow the outer lens 24 to be removed from the outer frame 66. To be in the unlocked position, the actuator bar 44 deflects at least a portion of the spring member 40 and the associated receptacles 42 in a direction away from the tabs 34 disengaging the hooks 38 from the receptacles 42. Once disengaged from both sides of the frame 22, the outer lens 24 can be removed from the frame 22.

Figure 13:
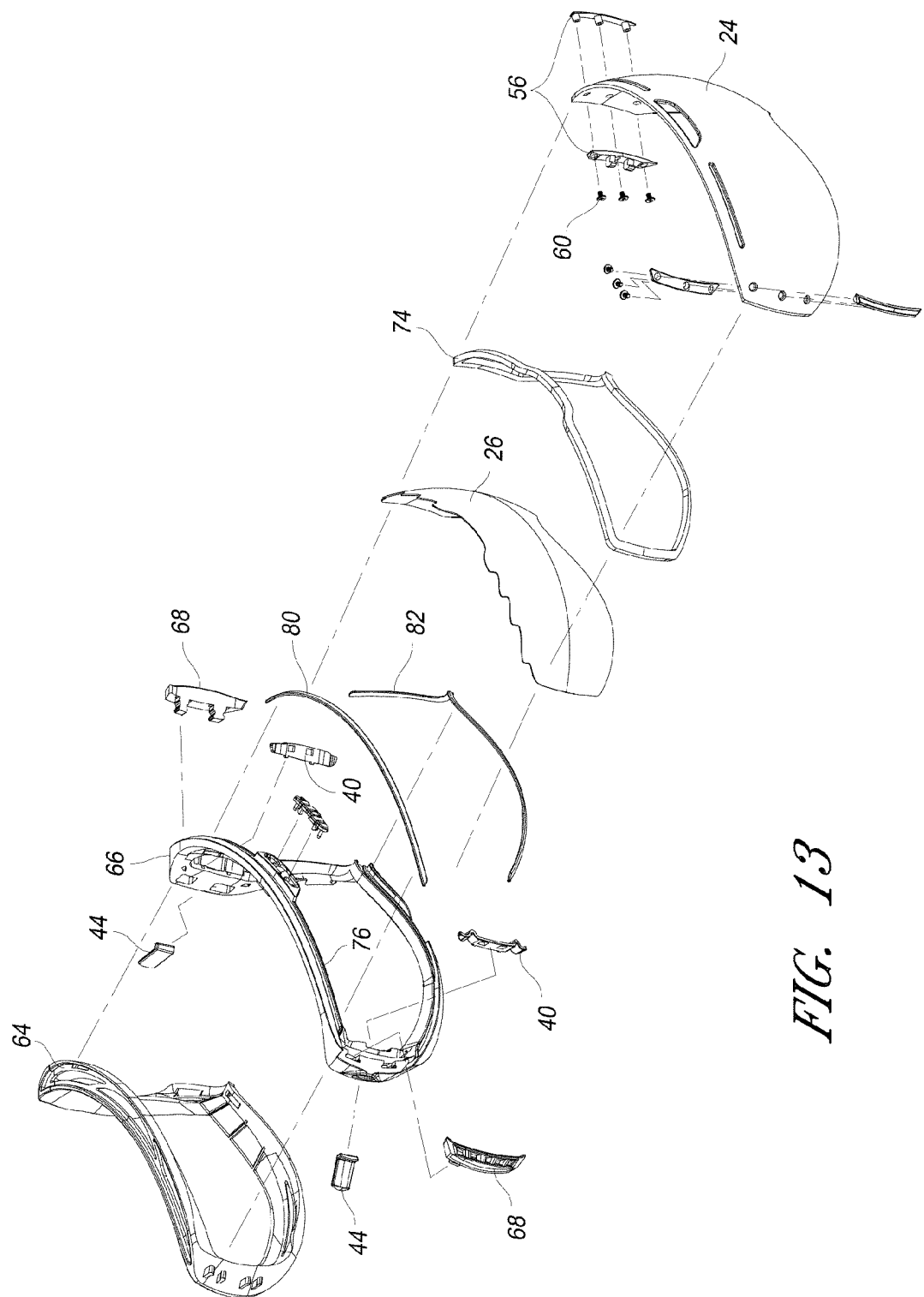
FIG. 13 is an exploded view of the sport goggle from FIG. 1 with the strap removed and showing the latching mechanism.

FIG. 13 is an exploded view of the sport goggle 20 from FIG. 1 with the strap 28 removed and showing the latching mechanism 32. As is illustrated in FIG. 13, the latching mechanism 32 secures the outer lens 24 in the frame 22 by inducing an interference fit between the lens 24 and frame 22. The interference fit may be induced by locking or otherwise allowing the latching mechanism 32 to close which imposes compressive and tensile forces on the outer lens 24 and frame 22, respectively. By contrast, opening/unlocking the latching mechanism 32 releases the applied forces thereby permitting removal of the outer lens 24 from the frame 22. Accordingly, the outer lens 24 may be removed without a user having to apply a force directly to the outer lens 24.

The inner lens 26 is also releasably retained within the frame 22. As illustrated in FIG. 13, the outer member 66 of the frame 22 may include receiving recesses 76. The recesses 76 may receive a tab 78 of the inner lens 26 and thereby assist in retaining and positioning the inner lens 26. One or more tracks 80, 82 provide a space for receiving and retaining the inner lens 26. In particular embodiments, the tracks 80, 82 have a curved profile which matches the outer profile of the edge of the inner lens 26. The tracks 80, 82 may facilitate the retention of the inner lens 26 by providing a constant retaining surface along the outer periphery of the inner lens 26.

FIG. 14 is a front perspective view of the spring member 40 of the latching mechanism 32. The spring member 40 is actuated by the actuator bar 44 illustrated in FIGS. 15 and 16.

As shown in FIG. 14, the spring member 40 may have one or two radially outward flared flanges 84 to aid in aligning the spring member 40 within the frame 22. Any suitable flare angle or flare shape may be used. The spring force exerted by the spring member 40 depends on the thickness and modulus of the material of which it is constructed. The force also depends on the precise wavy profile, i.e. the number, shape and size of the ridges 86. The spring member 40 may be made from a plastic, metal, or other material suitable for particular applications. The profile shown in FIG. 14, when formed out of plastic about 0.125 inches thick, provides sufficient flexibility for typical applications. A person having ordinary skill in the art would be able to alter the materials, material properties, ridge dimensions, number of ridges, flange angles, and/or spring member 40 thickness to optimize the spring member 40 for particular applications. The profile need not be perfectly symmetric and may be asymmetric as is illustrated in FIG. 14. The ridges 86 may be of different shapes or sizes. The ridges 86 need not be at the illustrated location but are disposed at a location which allows the actuator bar 44 to deflect at least a portion of the spring member 44 to allow the tabs 34 to disengage from the receptacles 42. The thickness of the spring member 40 may also vary in any direction.

To more fully illustrate the functionality associated with certain embodiments of the sports goggle 20, the following description of an example replacement of the outer lens 24 process is provided with reference to various components previously described and illustrated in FIGS. 1-16. To remove the outer lens 24, the process begins by sliding the actuator bar 44 to the unlocked position. As mentioned, sliding the actuator bar 44 to the unlocked position may require flexing at least a portion of the spring member 40. Once the spring member 40 is sufficiently flexed or bent, the spring member 40 is under a compressive load and wants to return to its initial unflexed or unbent position. When the spring member 40 is sufficiently flexed, the tab 34 is disengaged from the receptacle 42 thereby clearing a path for the tab 34 and attached outer lens 24 to exit the frame 22.

To replace the outer lens 24, the user releases the actuator bar 44. The spring member 40 returns to its unflexed position which slides the released actuator bar 44 in a direction away from the spring member 40. As the spring member 40 moves to the unflexed position, the associated receptacles 42 also move with the spring member 40. The outer lens 24 is then position over the frame 22 and then lowered onto the frame 22. At this point, the tabs 34 of the outer lens 24 enter the passages 48 until the hooks 38 on the tabs 34 abut an edge of the spring member 40. Slight pressure placed on the outer lens 24 towards the frame 22 causes the curved outer surface of the hook 38 to apply a force along an axis that is perpendicular to the direction along which pressure is being applied to the outer lens 24. The force being applied to the spring member 40 is parallel to the axis along which the actuator bar 44 slides between the locked and unlocked positions. This force flexes at least a portion of the spring member 40 in the region of the hook 38 until the hook 38 is able to pass by the edge of the spring member 40 and enter the receptacle 42. As the hook 38 enters the receptacle 42, the spring member 40 returns to its unflexed position and locks the hook 38 in the receptacle 42. While a particular lens replacement process has been described, it should be noted that certain steps may be rearranged, modified, or eliminated where appropriate.

Although the inventions have been disclosed in the context of a certain preferred embodiments and examples, it will be understood by those skilled in the art that the present disclosure extends beyond the specifically disclosed embodiments to other alternative embodiments and/or uses of the embodiments and obvious modifications and equivalents thereof. In addition, while a number of variations of the embodiments have been shown and described in detail, other modifications, which are within the scope of this disclosure, will be readily apparent to those of skill in the art based upon this disclosure. It is also contemplated that various combinations or subcombinations of the specific features and aspects of the embodiments may be made and still fall within the scope of the disclosure. Accordingly, it should be understood that various features and aspects of the disclosed embodiments can be combine with or substituted for one another in order to form varying modes of the disclosed embodiments. Thus, it is intended that the scope of the present disclosure should not be limited by the particular disclosed embodiments described above but by a fair reading of the claims which follow.

What is claimed is:

1. A sports goggle comprising:
a frame defining a field of view for a wearer;
a strap attachable to lateral ends of the frame and configured to circumscribe a head of the wearer;
a first lens attachable to the frame;
a second lens attachable to the frame and covering the first lens, the second lens having one or more first engagement members projecting away from an inner surface of the second lens; and
a second engagement member disposed on the frame and configured to selectively engage with the first engagement member, the second engagement member having a button surface and being movable between a locked position and an unlocked position, the second engagement member engaging with the first engagement member when in the locked position to prevent the second lens from being removed from the frame, the second engagement member disengaging from the first engagement member when the button surface is pressed by the wearer, wherein the second engagement member comprises a spring, the spring directly engaging with the one or more first engagement members when in the locked position.

2. The sports goggle of claim 1, wherein the one or more first engagement members are one or more tabs.

3. The sports goggle of claim 2, wherein each of the one or more tabs comprises a hook at a distal end, the hook being configured to engage with the one or more second engagement members.

4. The sports goggle of claim 2, wherein the second lens comprises four tabs, a pair of the four tabs being disposed in each temple region of the outer lens, and wherein the frame comprises corresponding passages configured to receive the four tabs.

5. The sports goggle of claim 3, wherein each hook comprises a portion which curves away from the tab.

6. The sports goggle of claim 1, wherein the one or more spring members comprise one or more receptacles.

7. The sports goggle of claim 6, wherein each of the one or more spring members comprises two receptacles.

8. The sports goggle of claim 1, wherein each of the one or more spring members comprises a flange.

9. The sports goggle of claim 1, wherein each of the one or more spring members comprises one or more ridges.

10. The sports goggle of claim 1, wherein the frame comprises two spring members, each spring member being disposed in each temple region of the frame.

11. The sports goggle of claim 1 wherein the frame has one or more recesses configured to receive an outer peripheral edge of the first lens.

12. The sports goggle of claim 1 further comprising a gasket disposed between the first lens and the second lens.

13. The sports goggle of claim 1, wherein the strap comprises a connector and the frame comprises a receiver, the receiver being sized to receive the connector.

14. A sports goggle comprising:
a frame defining a field of view for a wearer, the frame comprising an outer frame member releasably securable to an inner frame member, the outer frame member having a passage extending through a side of the outer frame, the inner frame member including one or more tangs extending from the inner frame member so as to enter the passage when the inner frame is secured to the outer frame; and
a strap having connectors at both ends of the strap, the connectors being attachable to lateral ends of the outer frame member, each connector having one or more projections, the projections being configured to enter the passage in the outer frame member from an opposite side from the one or more tangs to directly engage with the tangs of the inner frame member so as to prevent rotation of the connectors relative to their respective lateral ends of the outer frame.

15. A sports goggle comprising:
a frame defining a field of view for a wearer and having a spring member and an actuator bar, the actuator bar being disposed in the frame and slidable between a first position and a second position, the spring member being disposed in the frame so as to bend between a locked position and an unlocked position, the spring member being in the locked position when the actuator bar is in the first position and being in the unlocked position when the actuator bar is in the second position; and
a lens attachable to the frame and having one or more tabs projecting away from an inner surface of the lens, the tabs directly engaging with the spring member when the actuator bar is in the first position to prevent the lens from being removed from the frame, the tabs disengaging from the spring member when the actuator bar is slid to the second position.

16. The sports goggle of claim 15 further comprising a strap attachable to lateral ends of the frame and configured to circumscribe a head of the wearer.

17. The sports goggle of claim 15, wherein each of the one or more tabs comprises a hook at a distal end, the hook being configured to engage with the spring member.

18. The sports goggle of claim 15 further comprising an inner lens, the lens covering the inner lens and being separated from the inner lens by an air gap.

19. The sports goggle of claim 15, wherein the spring member comprises one or more receptacles for receiving at least a portion of the tab when the lens is secured to the frame and the spring is in the locked position.

\* \* \* \* \*